United States Patent [19]
Adedokun

[11] Patent Number: 5,910,151
[45] Date of Patent: Jun. 8, 1999

[54] INSTRUMENT FOR CLEANING THE TOP OF A TONGUE

[76] Inventor: Emmanuel A. Adedokun, 22327 W. 8 Mile Rd. B34, Detroit, Mich. 48219

[21] Appl. No.: 09/001,440

[22] Filed: Dec. 31, 1997

[51] Int. Cl.⁶ .................................................. A61B 17/24
[52] U.S. Cl. ............................................ 606/161; 606/162
[58] Field of Search .................................... 606/161, 162; D24/10, 23, 24, 28, 29, 33, 99

[56] References Cited

U.S. PATENT DOCUMENTS

| | | |
|---|---|---|
| D. 285,250 | 8/1986 | Andette ..................................... D24/23 |
| 1,851,396 | 3/1932 | Marbry ..................................... 606/161 |
| 4,083,103 | 4/1978 | Estandian ..................................... 30/47 |
| 5,095,621 | 3/1992 | Rapp ............................................. 30/90 |

*Primary Examiner*—Michael Buiz
*Assistant Examiner*—Vy Quang Bui

[57] ABSTRACT

A new instrument for cleaning the top of a tongue for cleaning the upper surface of a tongue. The inventive device includes a handle with an elongate arcuate head coupled to an end of the handle. A pair of side flanges extends from the head lower surface at opposite ends of the head. An elongate arcuate scraper member extends between the opposite ends of the head and extends away from the lower surface of the head. The scraper member includes a blade portion and an attachment portion and may be detachable.

18 Claims, 2 Drawing Sheets

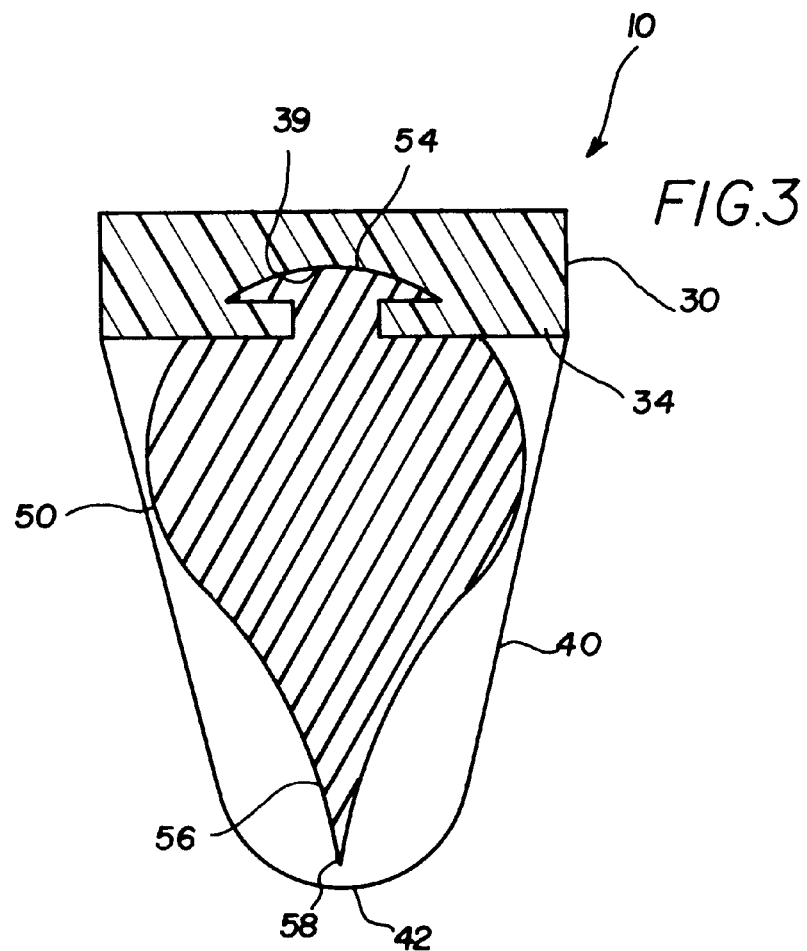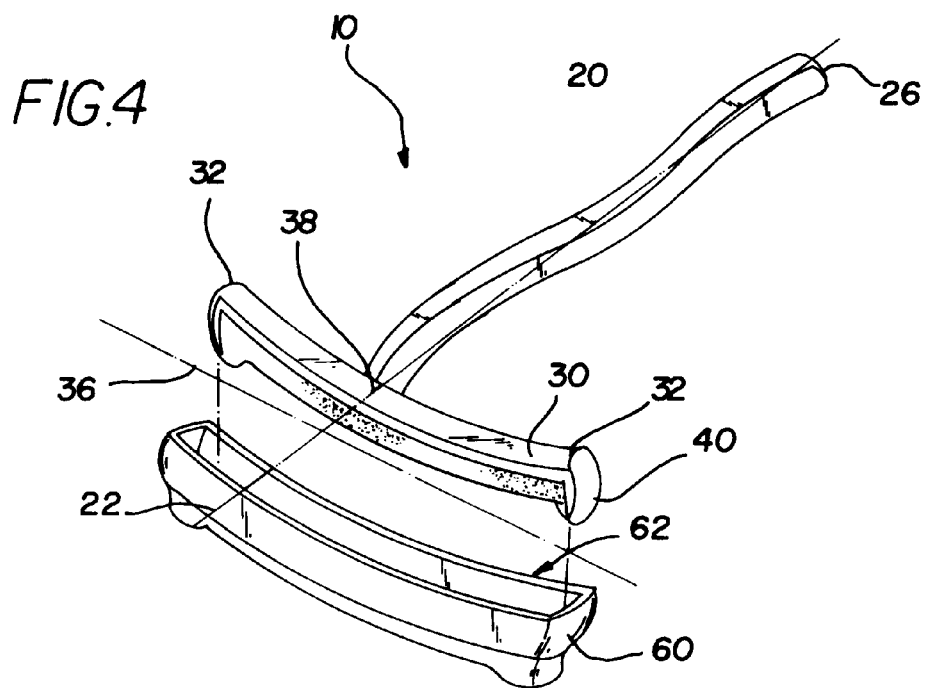

INSTRUMENT FOR CLEANING THE TOP OF A TONGUE

BACKGROUND OF THE INVENTION

1. Field of the Invention

The present invention relates to tongue cleaning instruments and more particularly pertains to a new instrument for cleaning the top of a tongue for cleaning the upper surface of a tongue.

2. Description of the Prior Art

The use of tongue cleaning instruments is known in the prior art. More specifically, tongue cleaning instruments heretofore devised and utilized are known to consist basically of familiar, expected and obvious structural configurations, notwithstanding the myriad of designs encompassed by the crowded prior art which have been developed for the fulfillment of countless objectives and requirements.

Known prior art tongue cleaning instruments include U.S. Pat. No. 5,282,814; U.S. Pat. No. Des. 265,506; U.S. Pat. No. Des. 360,262; U.S. Pat. No. Des. 285,250; U.S. Pat. No. 5,208,984; and U.S. Pat. No. Des. 267,508.

While these devices fulfill their respective, particular objectives and requirements, the aforementioned patents do not disclose a new instrument for cleaning the top of a tongue. The inventive device includes a handle with an elongate arcuate head coupled to an end of the handle. An elongate arcuate scraper member extends away from the lower surface of the head. A pair of side flanges extends from the head lower surface at opposite ends of the head.

In these respects, the instrument for cleaning the top of a tongue according to the present invention substantially departs from the conventional concepts and designs of the prior art, and in so doing provides an apparatus primarily developed for the purpose of cleaning the upper surface of a tongue.

SUMMARY OF THE INVENTION

In view of the foregoing disadvantages inherent in the known types of tongue cleaning instruments now present in the prior art, the present invention provides a new instrument for cleaning the top of a tongue construction wherein the same can be utilized for cleaning the upper surface of a tongue.

The general purpose of the present invention, which will be described subsequently in greater detail, is to provide a new instrument for cleaning the top of a tongue apparatus and method which has many of the advantages of the tongue cleaning instruments mentioned heretofore and many novel features that result in a new instrument for cleaning the top of a tongue which is not anticipated, rendered obvious, suggested, or even implied by any of the prior art tongue cleaning instruments, either alone or in any combination thereof.

To attain this, the present invention generally comprises a handle with an elongate arcuate head coupled to an end of the handle. An elongate arcuate scraper member extends away from the lower surface of the head. A pair of side flanges extends from the head lower surface at opposite ends of the head.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new instrument for cleaning the top of a tongue apparatus and method which has many of the advantages of the tongue cleaning instruments mentioned heretofore and many novel features that result in a new instrument for cleaning the top of a tongue which is not anticipated, rendered obvious, suggested, or even implied by any of the prior art tongue cleaning instruments, either alone or in any combination thereof.

It is another object of the present invention to provide a new instrument for cleaning the top of a tongue which may be easily and efficiently manufactured and marketed.

It is a further object of the present invention to provide a new instrument for cleaning the top of a tongue which is of a durable and reliable construction.

An even further object of the present invention is to provide a new instrument for cleaning the top of a tongue which is susceptible of a low cost of manufacture with regard to both materials and labor, and which accordingly is then susceptible of low prices of sale to the consuming public, thereby making such instrument for cleaning the top of a tongue economically available to the buying public.

Still yet another object of the present invention is to provide a new instrument for cleaning the top of a tongue which provides in the apparatuses and methods of the prior art some of the advantages thereof, while simultaneously overcoming some of the disadvantages normally associated therewith.

Still another object of the present invention is to provide a new instrument for cleaning the top of a tongue for cleaning the upper surface of a tongue.

Yet another object of the present invention is to provide a new instrument for cleaning the top of a tongue which includes a handle with an elongate arcuate head coupled to an end of the handle. An elongate arcuate scraper member extends away from the lower surface of the head. A pair of side flanges extends from the head lower surface at opposite ends of the head.

Still yet another object of the present invention is to provide a new instrument for cleaning the top of a tongue that includes a protective housing to prevent contamination of the scraper member.

Even still another object of the present invention is to provide a new instrument for cleaning the top of a tongue that provides a removable scraper member blade portion that may be readily interchanged.

Even still yet another object of the present invention is to provide a new instrument for cleaning the top of a tongue that scrapes the tongue, loosening and removing debris from the tongue.

Still yet even another object of the present invention is to provide a new instrument for cleaning the top of a tongue that promotes the oral hygiene of the tongue.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross sectional view of the present invention taken from line 3—3 of Figure.

FIG. 4 is a perspective view of the present invention particularly illustrating the protective housing.

DESCRIPTION OF THE PREFERRED EMBODIMENT

Figure 1:
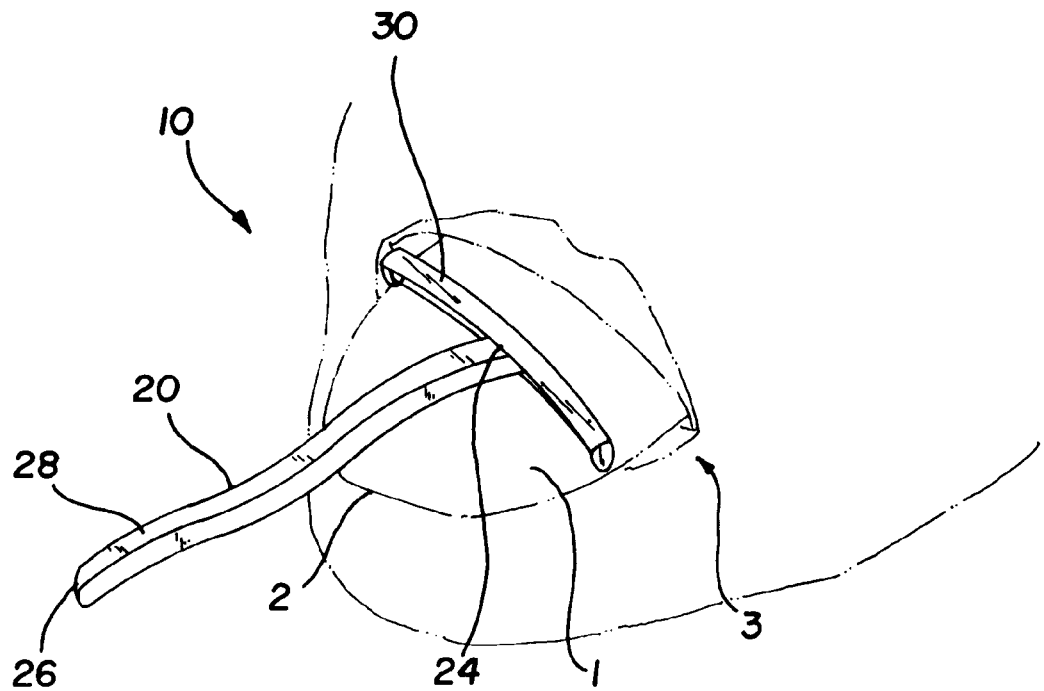
FIG. 1 is a perspective view of a new instrument for cleaning the top of a tongue according to the present invention in use.

With reference now to the drawings, and in particular to FIGS. 1 through 4 thereof, a new instrument for cleaning the top of a tongue embodying the principles and concepts of the present invention and generally designated by the reference numeral 10 will be described.

As best illustrated in FIGS. 1 through 4, the instrument for cleaning the top of a tongue 10 comprises a handle 20 with an elongate arcuate head 30 coupled to an end 24 of the handle 20. An elongate arcuate scraper member 50 extends away from the lower surface 34 of the head 30. A pair of side flanges 40 extends from the head lower surface 34 at opposite ends 32 of the head 30.

Preferably, as shown in FIG. 1, the handle 20 is elongate in length and has a longitudinal axis 22 extending through a proximal end 24 and a distal end 26 of the handle 20. A grasping portion 28 is located towards the handle distal end 26. In the preferred embodiment, the handle 20 is about five inches long.

Figure 2:
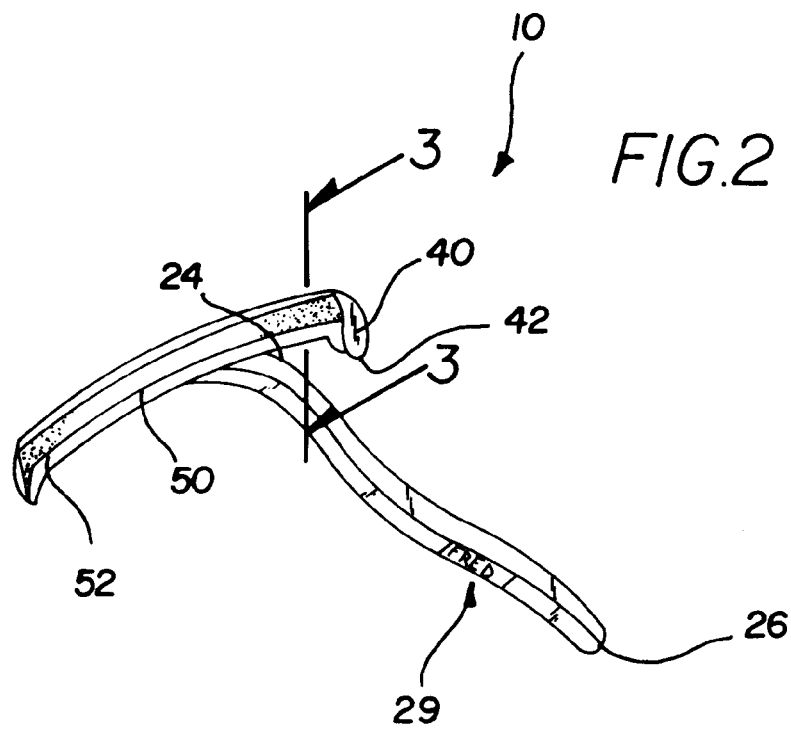
FIG. 2 is a perspective view of the present invention.

Preferably, the grasping portion 28 is arcuate in shape for easier grasping and better control. Also preferably, as shown in FIG. 2, the handle 20 has alpha-numeric indicia 29 thereon such as a name or an identification number. Ideally, the surface of the grasping portion 28 is coarse or covered with protrusions for better gripping. As an example, the surface of the grasping portion 28 may be covered with rubber nubs.

The elongate arcuate head 30 is coupled to the proximal end 24 of the handle 20 and has a pair of opposite ends 32 and a lower surface 34. Preferably, a tangential axis 36 that extends along a line tangent the midpoint 38 of the head 30 is aligned substantially perpendicular to the longitudinal axis 22 of the handle 20. Ideally, the handle proximal end 24 is coupled to the head 30 at the midpoint 38 of the head 30. In an ideal embodiment, the head 30 is about two inches long.

A side flange 40 is provided at each end 32 of the head 30. The flanges 40 each have a distal end 42 which extends from the lower surface 34 of the head 30. Preferably, as shown in FIGS. 2 and 3, each side flange distal end 42 extends from the head lower surface 34 further than the scraping edge 58 of the blade portion 56 extends from the head lower surface 34. Ideally, the side flanges 40 extend about ¼ to ¾ inch from the lower surface 34 of the head 30.

The elongate arcuate scraper member 50 extends between the head opposite ends 32 and includes a pair of opposite ends 52, an attachment portion 54 and an arcuate blade portion 56. The blade portion 56 extends between the scraper member opposite ends 52 and has a scraping edge 58. The scraping edge 58 of the blade portion 56 extends between the head opposite ends 32 and extends away from the lower surface 34 of the head 30. The attachment portion 54 is coupled to the lower surface 34 of the head 30.

In the preferred embodiment, as illustrated in FIG. 3, the attachment portion 54 is detachably coupled to the lower surface 34 of the head 30. In such an embodiment, a groove 39 in the head lower surface 34 extends between the head opposite ends 32. In use, the scraper member attachment portion 54 is slid along the groove 39 to attach it to the head lower surface 34.

In an optional embodiment, the scraping edge 58 of the scraping member blade portion 56 is constructed from the hooks portion (not shown) of a hooks and loops fastener. In such an embodiment, the elongate arcuate scraper member 50 extends between the head opposite ends 32 and includes a pair of opposite ends 52, an attachment portion 54 and an arcuate blade portion 56 constructed from the hooks portion (not shown) of a hooks and loops fastener. The blade portion 56 extends between the scraper member opposite ends 52. The hooks portion (not shown) of the blade portion 56 extends away from the lower surface 34 of the head 30 and extends between the head opposite ends 32. The scraper member attachment portion 54 is coupled to the lower surface 34 of the head 30.

In the preferred embodiment, a protective housing 60 is detachably coupled to the head 30. The protective housing 60 includes a cavity 62 into which the scraper member 50 and side flanges 40 are insertable. Preferably, the protective housing 60 engages the head 30 and the side flanges 40 to provide an airtight seal when the protective housing 60 is coupled to the head 30.

In use, the instrument for cleaning the top of a tongue is grasped by the grasping portion 28 of the handle 20. The head 30 is inserted into an open mouth 3 with the scraper member 50 facing the tongue 1. The scraper member blade portion 56 engages the tongue 1 and is moved towards the tip 2 of the tongue 1 so that the scraping edge 58 of the blade portion 56 scrapes the tongue 1, loosening and removing debris from the tongue 1.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An instrument for cleaning the top of a tongue, comprising:

a handle having longitudinal axis, a proximal end, a distal end, a grasping portion, said longitudinal axis being extended through said handle proximal end and said handle distal end, said grasping portion being located towards said handle distal end, wherein said handle has a uniform cross-section along a length thereof and is bent to define at least two arcuate undulations therein which extend in opposite directions;

an elongate arcuate head having a pair of opposite ends, and a lower surface, said handle proximal end being coupled to said head; and an elongate arcuate scraper member having a pair of opposite ends, an attachment portion and an arcuate scraping portion, said scraping portion having a scraping edge, said scraping portion being extended between said scraper member opposite ends, said scraper member being extended between said head opposite ends, said attachment portion being imbedded to said lower surface of said head, said scraping edge of said scraping portion being extended away from said lower surface of said head.

2. The instrument for cleaning the top of a tongue of claim 1, wherein said handle is elongate in length.

3. The instrument for cleaning the top of a tongue of claim 1, wherein said handle has alpha-numeric indicia thereon.

4. The instrument for cleaning the top of a tongue of claim 1, wherein said head has a midpoint and a tangential axis, said tangential axis being extended along a line tangent said midpoint of said head, said tangential axis being aligned substantially perpendicular to said longitudinal axis of said handle.

5. The instrument for cleaning the top of a tongue of claim 4, wherein said handle proximal end is coupled to said head at said midpoint.

6. The instrument for cleaning the top of a tongue of claim 1, wherein said attachment portion being detachably coupled to said lower surface of said head via a substantially T-shaped tongue and groove.

7. The instrument for cleaning the top of a tongue of claim 1, and further including a pair of side flanges each having a distal end, each said side flange being provided at each said end of said head, each said side flange distal end being extended from said lower surface of said head, wherein each said side flange distal end is extended from said head lower surface further than said scraping edge of said scraping portion is extended from said head lower surface.

8. The instrument for cleaning the top of a tongue of claim 7, further comprising a protective housing, said protective housing having a cavity, said scraping member and said side flanges being insertable into said cavity, said head being detachably coupled to said protective housing for affording a sealed compartment in which the scraping is removably positioned.

9. The instrument for cleaning the top of a tongue of claim 1, wherein said scraping edge of said scraping portion of said scraper member is constructed from the hooks portion of a hooks and loops fastener.

10. An instrument for cleaning the top of a tongue, comprising:

an elongate handle having longitudinal axis, a proximal end, a distal end, an arcuate grasping portion, said longitudinal axis being extended through said handle proximal end and said handle distal end, said grasping portion being located towards said handle distal end, said handle having alpha-numeric indicia thereon, wherein the handle has a uniform cross-section along a length thereof and is bent to define at least two arcuate undulations therein which extend in opposite directions;

an elongate arcuate head having midpoint, a tangential axis, a pair of opposite ends, and a lower surface, said tangential axis being extended along a line tangent said midpoint of said head, said handle proximal end being coupled to said head at said midpoint, said tangential axis being aligned substantially perpendicular to said longitudinal axis of said handle;

a pair of side flanges each having a distal end, each said side flange being provided at each said end of said head, each said side flange distal end being extended from said lower surface of said head;

an elongate arcuate scraper member having a pair of opposite ends, an attachment portion and an arcuate blade portion together having a tear drop-shaped configuration, said blade portion being constructed from the hooks portion of a hooks and loops fastener, said blade portion being extended between said scraper member opposite ends, said scraper member being extended between said head opposite ends, said attachment portion being detachably coupled to said lower surface of said head via a substantially T-shaped tongue and groove, said hooks portion of said blade portion being extended away from said lower surface of said head, each said side flange distal end being extended from said head lower surface further than said hooks portion of said blade portion;

wherein each of said side flange distal ends being extended from said lower surface of said head past a lower end of said blade arcuate blade portion; and a protective housing having a cavity defined by a bottom wall and a peripheral side wall coupled to a periphery of said bottom wall and extending upwardly therefrom, said scraping member and said side flanges being insertable into said cavity, said head being detachably coupled to said protective housing for affording a sealed compartment in which said scraping member is removably positioned.

11. An instrument for cleaning the top of a tongue, comprising:

a handle having longitudinal axis, a proximal end, a distal end, a grasping portion, said longitudinal axis being extended through said handle proximal end and said handle distal end, said grasping portion being located towards said handle distal end;

an elongate arcuate head having a pair of opposite ends, and a lower surface, said handle proximal end being coupled to said head; and an elongate arcuate scraper member having a pair of opposite ends, an attachment portion and an arcuate blade portion, said blade portion having a scraping edge, said blade portion being extended between said scraper member opposite ends, said scraper member being extended between said head opposite ends, said attachment portion being removably coupled to said lower surface of said head via a substantially T-shaped tongue and groove, said scraping edge of said blade portion being extended away from said lower surface of said head;

wherein said scraping edge of said blade portion of said scraper member is constructed from the hooks portion of a hooks and loops fastener.

12. The instrument for cleaning the top of a tongue of claim 11, wherein said handle is elongate in length.

13. The instrument for cleaning the top of a tongue of claim 11, wherein said grasping portion of said handle is arcuate in shape.

14. The instrument for cleaning the top of a tongue of claim 11, wherein said handle has alpha-numeric indicia thereon.

15. The instrument for cleaning the top of a tongue of claim 11, wherein said head has a midpoint and a tangential axis, said tangential axis being extended along a line tangent said midpoint of said head, said tangential axis being aligned substantially perpendicular to said longitudinal axis of said handle.

16. The instrument for cleaning the top of a tongue of claim 11, wherein said attachment portion being detachably coupled to said lower surface of said head via a T-shaped tongue and groove combination.

17. The instrument for cleaning the top of a tongue of claim 11, and further including a pair of side flanges each having a distal end, each said side flange being provided at each said end of said head, each said side flange distal end being extended from said lower surface of said head, wherein each said side flange distal end is extended from said head lower surface further than said scraping edge of said blade portion is extended from said head lower surface.

18. The instrument for cleaning the top of a tongue of claim 17, further comprising a protective housing, said protective housing having a cavity, said scraping member and said side flanges being insertable into said cavity, said head being detachably coupled to said protective housing for affording a sealed compartment in which the blade is removably positioned.

* * * * *